(12) United States Patent
Jin et al.

(10) Patent No.: US 7,223,790 B2
(45) Date of Patent: May 29, 2007

(54) DIMERIC COMPOUNDS AND THEIR USE AS ANTI-VIRAL AGENTS

(75) Inventors: Betty Jin, Mount Waverley (AU); Simon J. F. MacDonald, Stevenage (GB); Darryl McConnell, Vienna (AT); Van T. T. Nguyen, Noble Park (AU); Stephen E. Shanahan, Stevenage (GB); Wen-Yang Wu, Mount Waverley (AU)

(73) Assignee: Biota Scientific Management Pty Ltd., Victoria (AU)

( * ) Notice: Subject to any disclaimer, the term of this patent is extended or adjusted under 35 U.S.C. 154(b) by 185 days.

(21) Appl. No.: 10/494,260

(22) PCT Filed: Nov. 8, 2002

(86) PCT No.: PCT/AU02/01527

§ 371 (c)(1),
(2), (4) Date: Nov. 3, 2004

(87) PCT Pub. No.: WO03/040137

PCT Pub. Date: May 15, 2003

(65) Prior Publication Data

US 2005/0054719 A1 Mar. 10, 2005

(30) Foreign Application Priority Data

Nov. 9, 2001 (AU) .................................... PR8794

(51) Int. Cl.
*A61K 31/35* (2006.01)
(52) U.S. Cl. .................. 514/459; 549/424; 549/425
(58) Field of Classification Search ............... 549/424, 549/425; 514/459
See application file for complete search history.

(56) References Cited

U.S. PATENT DOCUMENTS 6,548,476 B1 * 4/2003 Wu et al. .................... 514/2

FOREIGN PATENT DOCUMENTS

| WO | WO 98/21243 | 5/1998 |
| WO | WO 00/55149 A1 | 9/2000 |
| WO | WO 02/20514 A1 | 3/2002 |

OTHER PUBLICATIONS

Fleming, DM 'Managing influenza: amantadine, rimantadine and beyond' PMID: 11351773, (2001).*
Supplementary European Search Report of EP 02 77 1913.

* cited by examiner

*Primary Examiner*—Amelia A. Owens
(74) *Attorney, Agent, or Firm*—Foley & Lardner LLP

(57) ABSTRACT

The invention relates to compounds of general formula (I); in which R is an amino or guanidino group; $R^2$ is acetyl or trifluoroacetyl; X is CONH, NHCO or O; n is an integer from 2 to 6; and Y is $C_2$–$C_8$ alkyl $C_{3-8}$ cycloalkyl, $C_1$–$C_4$ alkoxyalkyl, an amino acid or dipeptide, or a pharmaceutically acceptable derivative thereof, methods for their preparation, pharmaceutical formulations containing them or their use in the prevention or treatment of a viral infection

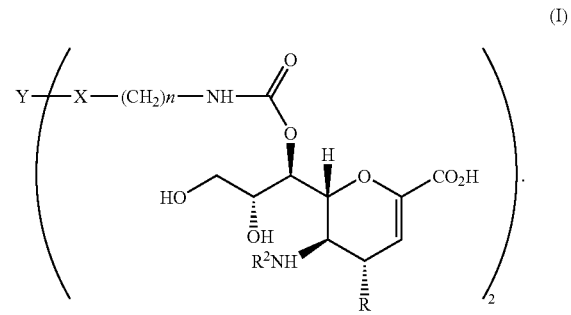

15 Claims, No Drawings

DIMERIC COMPOUNDS AND THEIR USE AS ANTI-VIRAL AGENTS

This invention relates to new chemical compounds and their use in medicine. In particular the invention concerns novel dimeric compounds, methods for their preparation, pharmaceutical formulations thereof and their use as anti-viral agents.

BACKGROUND OF THE INVENTION

Enzymes with the ability to cleave N-acetyl neuraminic acid (NANA), also known as sialic acid, from other carbohydrates are present in many microorganisms. These include bacteria such as *Vibrio cholerae, Clostridium perfringens, Streptococcus pneumoniae* and *Arthrobacter sialophilus*, and viruses such as influenza virus, parainfluenza virus, mumps virus, Newcastle disease virus and Sendai virus. Most of these viruses are of the orthomyxovirus or paramyxovirus groups, and carry a neuraminidase activity on the surface of the virus particles. Many of these neuraminidase-possessing organisms are major pathogens of man and/or animals, and some, such as influenza virus and Newcastle disease virus, cause diseases of enormous importance.

It has long been thought that inhibitors of neuraminidase might prevent infection by neuraminidase-bearing viruses. Most of the known neuraminidase inhibitors are analogues of neuraminic acid, such as 2-deoxy-2,3-dehydro-N-acetylneuraminic acid (DANA) and some of its derivatives (Meindl et al, Virology, 1974 58 457). Our International Patent Publication No. WO 91/16320 describes a number of analogues of DANA which are active against viral neuraminidase, and it has been shown in particular that 4-guanidino-2-deoxy-2,3-dehydro-N-acetylneuraminic acid (Compound (A), code number GG167) is useful in the treatment of influenza A and B (N. Engl. J. Med., 1997 337 874–880). Other patent applications describe various closely-related sialic acid derivatives (eg. PCT Publications No. WO 95/18800, No. WO 95/20583 and No. WO 98/06712), and anti-viral macromolecular conjugates of GG167 have also been described (International Patent Application No. PCT/AU97/00771).

Compound (A)

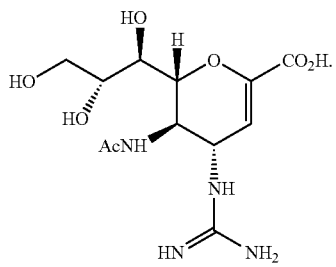

Ac represents acetyl

International Patent Publication No. WO 00/55149, describes dimeric compounds which comprise two neuraminidase binding molecules, such as compound (A), attached to a common spacer or linking group of up to 100 atoms in length.

We have now discovered a novel class of compounds which fall within the generic scope of International Patent Publication No. WO 00/55149, but which are not specifically disclosed therein, and exhibit a surprisingly advantageous anti-influenza activity profile which includes a long lung residency time and high potency.

Without wishing to be bound by theory, the basis for the long residency time in the lungs is thought to be due to the size and molecular weight of the compounds preventing entry through tight junctions in the respiratory epithelium and the polarity of the compounds being such that passage through the cell membranes occurs very inefficiently. An alternative theory is that the compounds themselves interact with the phospholipids in the cell membrane or other components of the respiratory epithelium and increase the residency time in the lungs.

SUMMARY OF THE INVENTION

In a first aspect, the present invention provides for a compound of general formula (I):

(I)

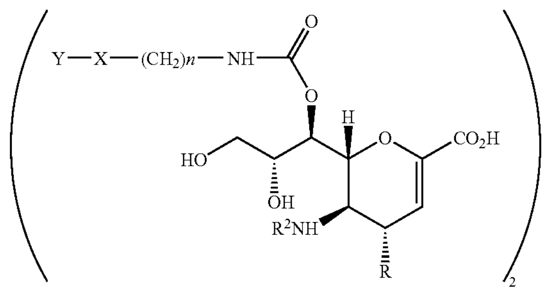

in which

R is an amino or guanidino group;

$R^2$ is acetyl or trifluoroacetyl;

X is CONH, NHCO or O;

n is an integer from 2 to 6; and

Y is $C_2$–$C_8$ alkyl $C_{3-8}$ cycloalkyl, $C_1$–$C_4$ alkoxyalkyl, an amino acid or dipeptide, or a pharmaceutically acceptable derivative thereof, with the proviso that when R is a guanidino group, $R^2$ is acetyl, X is O and n is 2, then Y is not $C_2$ alkyl.

Preferably R is a guanidino group.

Preferably $R^2$ is an acetyl group.

The term "$C_2$–$C_8$ alkyl" refers to straight chain or branched chain hydrocarbon groups having from 2 to 8 carbon atoms. Illustrative of such alkyl groups are methyl, ethyl, propyl, isopropyl, butyl, isobutyl, sec-butyl, tert-butyl, pentyl, neopentyl, hexyl, heptyl and octyl.

As used herein, the term "$C_3$–$C_8$ cycloalkyl" refers to an alicyclic group having from 3 to 8 carbon atoms. Illustrative of such cycloalkyl groups are cyclopropyl, cyclobutyl, cyclopentyl and cyclohexyl.

As used herein the term "$C_1$–$C_4$ alkoxyalkyl" refers to straight chain or branched chain alkoxy groups having from 1 to 4 carbon atoms. Illustrative of such alkoxy groups are methoxy, ethoxy, propoxy, isopropoxy, butoxyl, isobutoxy, sec-butoxy and tert-butoxy.

The term "amino acid" is used herein in its broadest sense and refers to α-amino substituted carboxylic acids which are the building blocks of proteins such as the 20 standard amino acids as listed at page 96 of "Principles of Biochemistry" by Albert L. Lehninger (Worth Publishers, Inc. 1982).

The term "dipeptide" is used herein in its broadest sense and refers to two amino acids linked by a peptide bond (also called an amide bond). Examples include glutamic-glycine, glycine-glycine or aspartic-glycine.

It will be appreciated by those skilled in the art that the compounds of formula (I) may be modified to provide pharmaceutically acceptable derivatives thereof at any one or more of the functional groups in the compounds of formula (I). Of particular interest as such derivatives are compounds modified at the carboxyl function, hydroxyl functions or at amino groups. Thus compounds of interest include alkyl esters, such as methyl, ethyl, propyl or isopropyl esters, aryl esters, such as phenyl, benzoyl esters, and acetyl esters of the compounds of formula (I).

The term "pharmaceutically acceptable derivative" means any pharmaceutically acceptable salt, ether, ester or salt of such ester of a compound of formula (I) or any other compound which, upon administration to the recipient, is capable of providing a compound of formula (I) or an anti-virally active metabolite or residue thereof. Of particular interest as derivatives are compounds modified at the sialic acid carboxy or glycerol hydroxy groups, or at amino and guanidine groups.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic acid, while not in themselves pharmaceutically acceptable, may be useful in the preparation of salts useful as intermediates in obtaining compounds of the invention and their pharmaceutically acceptable acid addition salts.

Nuts (John Wiley & Sons, 1991). Pharmaceutically acceptable salts of the compounds of formula (I) may be prepared according to known procedures.

For ease of processing and preparation, it is preferable that the compounds of formula (I) are in crystalline form.

Accordingly, the present invention also provides a method for the preparation of the compound of formula (I) as defined above when X is CONH or NHCO, which comprises the steps of (a) coupling a compound of formula (II)

(II)

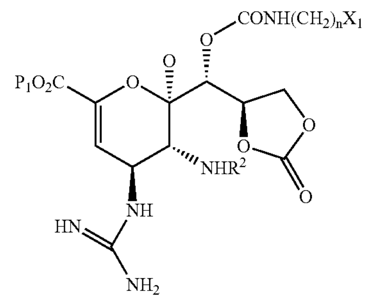

in which $R^2$ and n are as defined above, $P_1$ is a carboxylic acid protecting group and $X_1$ is $NH_2$ or $CO_2H$;

with a compound of formula (III)

$$X_2—Y—X_2 \quad (III)$$

in which Y is as defined above and $X_2$ is $CO_2H$ or $NH_2$ provided that it is not the same as $X_1$ to form a compound of formula (IV)

(IV)

and (b) deprotecting the compound of formula (IV).

Salts derived from appropriate bases include alkali metal (eg. sodium), alkaline earth metal (eg. magnesium), ammonium, and $NR_4^+$ (where R is $C_{1-4}$alkyl) salts.

The compounds of the invention may be prepared by methods described herein. It will be apparent to those skilled in the art, that it is necessary to use protecting groups to protect one or more functional groups of the neuraminidase binding molecule during the process of attaching the monomers to the alkyl spacer group. See for example "Protective Groups in Organic Synthesis" by T. W. Green and P. G. M.

The compounds of formula (I) possess antiviral activity. In particular these compounds are inhibitors of viral neuraminidase of orthomyxoviruses and paramyxoviruses, for example the viral neuraminidase of influenza A and B, parainfluenza, mumps and Newcastle disease.

Thus in a second aspect the invention provides a compound of formula (I) or a pharmaceutically acceptable derivative thereof, for use as an active therapeutic agent in the treatment of a viral infection, for example orthomyxovirus and paramyxovirus infections.

In a third aspect the invention provides a method for the prevention or treatment of a viral infection comprising the step of administration to a subject in need thereof of an effective amount of a compound of formula (I), or a pharmaceutically acceptable salt or derivative thereof.

Preferably, the viral infection is an orthomyxovirus or paramyxovirus infection. More preferably the viral infection is an influenza A or B infection.

Preferably the subject is an animal such as a mammal, more preferably a human, or a member of the genus *Equus*, for example a horse, donkey or mule. Most preferably the mammal is a human.

In a fourth aspect the invention provides use of a compound of the invention for the manufacture of a medicament for the treatment of a viral infection.

As used herein, the term "effective amount" is meant an amount of the compound of formula I effective to preventing or treating a viral infection in order to yield a desired therapeutic response. For example, to overcome or alleviate the effects of a viral infection.

The term "therapeutically-effective amount" means an amount of the compound of formula I to yield a desired therapeutic response. For example, treating or preventing a viral infection.

The specific "therapeutically-effective amount" will, obviously, vary with such factors as the particular viral infection being treated, the physical condition of the subject, the type of animal being treated, the duration of the treatment, the nature of concurrent therapy (if any), and the specific formulation employed and the structure of the compound or its derivatives.

Generally, the terms "treating", "treatment" and the like are used herein to mean affecting a subject, tissue or cell to obtain a desired pharmacologic and/or physiologic effect. The effect may be prophylactic in terms of completely or partially preventing a viral infection or sign or symptom thereof, and/or may be therapeutic in terms of a partial or complete cure of a viral infection. "Treating" as used herein covers any treatment of, or prevention of a viral infection in a vertebrate, a mammal, particularly a human, and includes: (a) preventing the viral infection from occurring in a subject that may be predisposed to the viral infection, but has not yet been diagnosed to the viral infection, but has not yet been diagnosed as having it; (b) inhibiting the viral infection, ie., arresting its development; or (c) relieving or ameliorating the effects, i.e., cause regression of the symptoms of the viral infection.

The compounds of the invention may also be used in diagnostic methods, in particular methods for the detection of influenza virus. For use in such methods it may be advantageous to link a compound of the invention to a label, such as a radioactive, fluorescent or chemiluminescent label.

Methods of diagnosis for which the compounds of the invention are suitable are described, for example, in our earlier applications PCT/AU97/00109 and PCT/AU97/00771.

In a fifth aspect the invention provides a method for the detection of a viral infection which comprises the step of contacting the compound of the invention with a sample suspected of containing the virus.

It will be further appreciated that the amount of a compound of the invention required for use in treatment will vary not only with the particular compound selected but also with the route of administration, the nature of the condition being treated, and the age and condition of the patient, and will ultimately be at the discretion of the attendant physician or veterinarian. In general however, a suitable dose will be in the range of from about 0.001 to 100 mg/kg of bodyweight per day, preferably in the range of 0.01 to 10 mg/kg/day, most preferably in the range of 0.1 to 1 mg/kg/day.

Treatment is preferably commenced before or at the time of infection and continued until virus is no longer present in the respiratory tract. However the compounds are also effective when given post-infection, for example after the appearance of established symptoms.

Suitably treatment is given on one or two occasions, preferably only once only for treatment, and preferably once per week for prophylaxis.

The compound is conveniently administered in unit dosage form, for example containing 1 to 100 mg, more conveniently 1 to 20 mg of active ingredient per unit dosage form.

While it is possible that, for use in therapy, a compound of the invention may be administered as the raw chemical, it is preferable to present the active ingredient as a pharmaceutical formulation.

Thus in a sixth aspect the invention provides a pharmaceutical formulation comprising a compound of formula (I) or a pharmaceutically acceptable salt or derivative thereof, together with one or more pharmaceutically acceptable carriers therefor and, optionally, other therapeutic and/or prophylactic ingredients. The carrier(s) must be "acceptable" in the sense of being compatible with the other ingredients of the formulation and not being deleterious to the recipient thereof.

The compounds of the invention may also be used in combination with other therapeutic and/or prophylactic agents, for example other anti-infective agents. In particular the compounds of the invention may be employed with other antiviral agents. The invention thus provides in a seventh aspect a combination comprising a compound of formula (I) or a pharmaceutically acceptable salt or derivative thereof together with another therapeutically and/or prophylactically active agent, in particular an antiviral agent.

The combinations referred to above may conveniently be presented for use in the form of a pharmaceutical formulation and thus such formulations comprising a combination as defined above together with a pharmaceutically acceptable carrier therefore comprise a further aspect of the invention.

Suitable therapeutic and/or prophylactic agents for use in such combinations include other anti-infective agents, in particular anti-bacterial and anti-viral agents such as those used to treat respiratory infections. For example, other compounds or vaccines effective against influenza viruses, such as the sialic acid analogues referred to above, e.g. zanamivir, oseltamivir, amantadine, rimantadine and ribavirin and FluVax, may be included in such combinations.

The individual components of such combinations may be administered either separately, sequentially or simultaneously in separate or combined pharmaceutical formulations.

When the compounds of the invention are used with a second therapeutic and/or prophylactic agent active against the same virus, the dose of each compound may either be the same as or different from that employed when each compound is used alone. Appropriate doses will be readily appreciated by those skilled in the art.

Pharmaceutical formulations include those suitable for oral, rectal, nasal, topical (including buccal and sub-lingual), vaginal or parenteral (including intramuscular, sub-cutaneous and intravenous) administration, or those in a form suitable for administration to the respiratory tract (including the nasal passages) for example by inhalation or insufflation. The formulations may, where appropriate, be conveniently presented in discrete dosage units, and may be prepared by any of the methods well known in the art of pharmacy. These methods include the step of bringing into association the active compound with liquid carriers or finely divided solid carriers or both, and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may for example be in the form of aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles, which may include edible oils, or preservatives.

The compounds according to the invention may also be formulated for parenteral administration by injection, for example bolus injection, or continuous infusion, and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulating agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base, and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and gum acacia or gum tragacanth; pastilles comprising the active ingredient in an inert base such as gelatin or sucrose and gum acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping moulds.

Formulations suitable for vaginal administration may be presented as pessaries, tampons, creams, gels, pastes, foams or sprays containing in addition to the active ingredient such carriers as are known in the art to be appropriate.

For administration to the respiratory tract, including intranasal administration, the neuraminidase inhibitors may be administered by any of the methods and formulations employed in the art for administration to the respiratory tract.

Thus in general the compounds may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethylene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of drug may be controlled by provision of a metered valve.

Alternatively the compounds may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form, for example in capsules or cartridges of eg. gelatin, or blister packs from which the powder may be administered by means of an inhaler.

In formulations intended for administration to the respiratory tract, including intranasal formulations, the compound will generally have a small particle size, for example of the order of 5 microns or less. Such a particle size may be obtained by means known in the art, for example by micronisation.

When desired, formulations adapted to give sustained release of the active ingredient may be employed.

Preferably the compounds of the invention are administered to the respiratory tract by inhalation, insufflation or intranasal administration, or a combination thereof.

"Relenza" is administered by oral inhalation as a free-flow powder via a "Diskhaler" (trade marks of the Glaxo-SmithKline group of companies). A similar formulation would be suitable for the present invention.

Thus, according to an eighth aspect of the present invention there is provided an inhaler which contains a formulation as defined above.

It will be appreciated that the inhaler may also be in the form of a meter dose aerosol inhaler.

For the purposes of this specification it will be clearly understood that the word "comprising" means "including but not limited to", and that the word "comprises" has a corresponding meaning.

All publications, including but not limited to patents and patent applications, cited in this specification are herein incorporated by reference as if each individual publication were specifically and individually indicated to be incorporated by reference herein as though fully set forth.

DETAILED DESCRIPTION OF THE INVENTION

The invention will now be described in detail by way of reference only to the following non-limiting examples.

TABLE 1

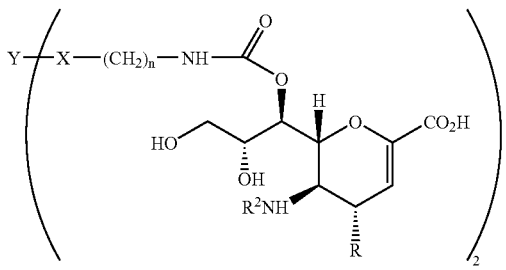

in which $R^2$ is acetyl and R is guanidine

| Compound No. | Y | X | n |
|---|---|---|---|
| 1 | $(CH_2)_8$ | CONH | 6 |
| 2 | $(CH_2)_4$ | CONH | 6 |
| 3 | $(CH_2)_2$ | CONH | 6 |
| 4 | $CH_2OCH_2$ | CONH | 6 |
| 5 | $(CH_2)_3$ | CONH | 6 |
| 6 | $(CH_2)_5$ | CONH | 6 |
| 7 | $(CH_2)_6$ | CONH | 6 |
| 8 | $(CH_2)_7$ | CONH | 6 |
| 9 | $(CH_2)_2$ | CONH | 3 |
| 10 | 5-Norbornene-2,3-diacid | CONH | 6 |
| 11 | $(CH_2)_2$ | CONH | 3 |
| 12 | $CH_2CH_2CH(NH_2)CONHCH_2$ (Glutamic-glycine) | CONH | 3 |
| 13 | $CH(NH_2)CH_2CH_2$ (Glutamic) | CONH | 3 |
| 14 | $CH(NH_2)CH_2$ (Aspartic) | CONH | 3 |
| 15 | $(CH_2)_3$ | NHCO | 2 |
| 16 | $CH_2CH_2OCH_2CH_2$ | NHCO | 2 |
| 17 | $(CH_2)_2$ | NHCO | 2 |
| 18 | $(CH_2)_6$ | NHCO | 2 |
| 19 | $(CH_2)_4$ | NHCO | 1 |
| 20 | $(CH_2)_6$ | NHCO | 1 |
| 21 | $(CH_2)_4$ | CONH | 3 |
| 22 | $(CH_2)_5$ | CONH | 3 |
| 23 | $(CH_2)_6$ | CONH | 3 |
| 24 | $(CH_2)_7$ | CONH | 3 |
| 25 | $(CH_2)_8$ | CONH | 3 |

Machine Methods

Green Method (LC/MS)

Micromass Platform II mass spectrometer operating in positive ion electrospray mode, mass range 100–1000 amu.
Column: 3.3 cm×4.6 mm ID, 3 μm ABZ+PLUS
Flow Rate: 3 ml/min
Injection Volume: 5 μl
Solvent A: 95% acetonitrile+0.05% formic acid
Solvent B: 0.1% formic acid+10 mMolar ammonium acetate
Gradient: 0% A/0.7 min, 0–100% A/3.5 min, 100% A/1.1 min, 100–0% A/0.2 min Purple Method (Mass Directed Autoprep HPLC)

The prep column used was a Supelcosil ABZplus (10 cm×2.12 cm)
UV wavelength: 200–320 nM
Flow: 20 ml/min
Injection Volume: 1 ml
Solvent A: 0.1% formic acid
Solvent B: 95% acetonitrile+5% formic acid
Gradient: 100% A/1 min, 100–80% A/9 min, 80–1% A/3.5 min, 1% A/1.4 min, 1–100% A/0.1 min Turquoise Method (Autoprep HPLC)

The prep column used was a Supelcosil ABZplus (10 cm×2.12 cm).
UV wavelength: 230 nm
Flow: 4 ml/min
Injection Volume: 2 ml
Solvent A: acetonitrile+0.05% TFA
Solvent B: water+0.1% TFA Method A(LC/MS)

Micromass Platform II mass spectrometer operating in positive ion electrospray mode, mass range 100–1000 amu.
Column: 3.3 cm×4.6 mm ID, 3 μm ABZ+PLUS
Flow Rate: 3 ml/min
Injection Volume: 5 μl
Solvent A: 95% acetonitrile+0.05% formic acid
Solvent B: 0.1% formic acid+10 mMolar ammonium acetate
Gradient: 0% A/0.7 min, 0–100% A/3.5 min, 100% A/1.1 min, 100–0% A/0.2 min Method B (LC/MS)

Waters ZQ mass spectrometer operating in positive ion electrospray mode, mass range 100–1000 amu.
Column: 3.3 cm×4.6 mm ID, 3 μm ABZ+PLUS
Flow Rate: 3 ml/min
Injection Volume: 5 μl
Solvent A: 95% acetonitrile+0.05% formic acid
Solvent B: 0.1% formic acid+10 mMolar ammonium acetate
Gradient: 0% A/0.7 min, 0–100% A/3.5 min, 100% A/1.1 min, 100–0% A/0.2 min Method C (Autoprep HPLC)

The prep column used was a Supelcosil ABZplus (10 cm×2.12 cm).
UV wavelength: 230 nm
Flow: 4 ml/min
Injection Volume: 2 ml
Solvent A: acetonitrile+0.05% TFA
Solvent B: water+0.1% TFA
Gradient: 0–40% A/20 min, 40% A/20 min, 40–100% A/0.3 min, 100% A/15 min, 100–0% A/3 min Method D (Mass Directed Autoprep HPLC)

The prep column used was a Supelcosil ABZplus (10 cm×2.12 cm)
UV wavelength: 200–320 nM
Flow: 20 ml/min
Injection Volume: 1 ml
Solvent A: 0.1% formic acid
Solvent B: 95% acetonitrile+5% formic acid
Gradient: 100% A/1 min, 100–80% A/9 min, 80–1% A/3.5 min, 1% A/1.4 min, 1–100% A/0.1 min Abbreviations
EtOAc ethyl acetate
MeOH methanol HPLC high pressure liquid chromatography
SPE solid phase extraction
LC/MS Liquid chromatography/mass spectroscopy
DMF N,N-Dimethylformamide
WSCDI 1-(3-Dimethylaminopropyl)-3-ethylcarbodiimide methiodide
HOBt 1-hydroxybenzotriazole
DIPEA N,N-diisopropylethylamine
MeCN acetonitrile
RT room temperature
EtOAc ethyl acetate
MgSO₄ magnesium sulphate
DMF dimethylformamide dried by azeotroping 3 times from anhydrous toluene and then dissolved in anhydrous acetonitrile (20 ml) with the addition of a few 3 angstrom molecular sieve pellets. The stirred solution was treated with N-tert-butoxycarbonyl 1,4-diaminobutane (0.72 g, 3.8 mmol) and triethylamine (0.43 g, 4.2 mmol). The mixture was stirred for 16 h under a nitrogen atmosphere. Volatiles were removed in vacuo to afford a yellow residue. This was redissolved in EtOAc (50 ml), washed with 0.5 MHCl (30 ml) then brine (30 ml). The solution was dried ($Na_2SO_4$) and solvent evaporated in vacuo to afford a cream coloured foam. Further purification was by Biotage flash chromatography, eluant initially Intermediate 1

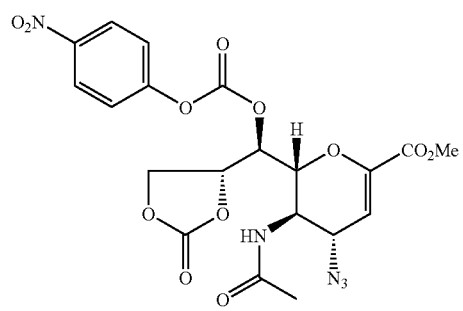
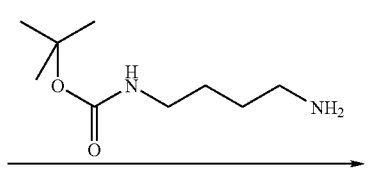

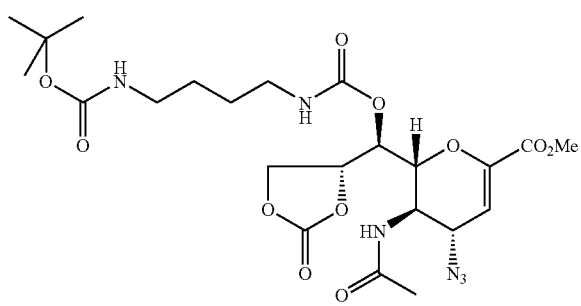

Intermediate 1

(4S, 5R, 6R)-5-Acetylamino-4-azido-6-[(S)-4-nitrophenoxycarbonyloxy)-(2-oxo-[1,3]dioxolan-4R-yl)-methyl]-5,6-dihydro-4H-pyran-2-carboxylic acid methylester (see *Eur. J. Med. Chem.* 1999, 34, 563–574) (2.00 g, 3.8 mmol) was EtOAc: Cyclohexane (1:1) then EtOAc. Evaporation of solvent in vacuo gave Intermediate 1 (1.26 g, 58% yield) as a white solid. LC/MS (Method B) showed $MH^+$=571; $T_{RET}$=2.87 min Intermediate 2

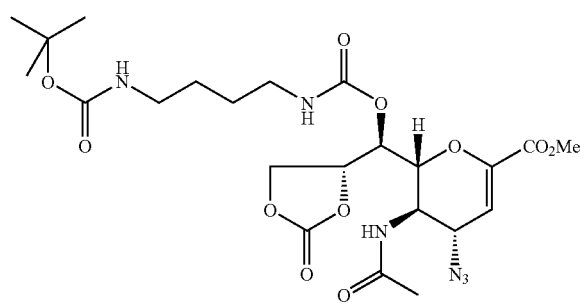

Intermediate 1

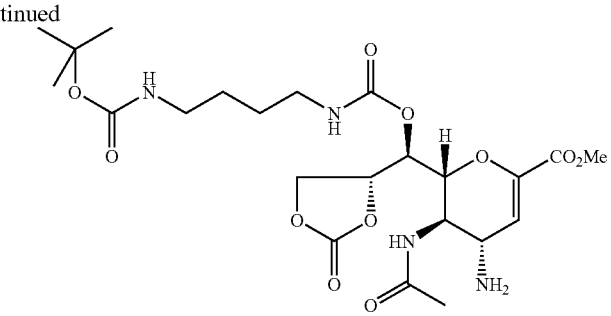

Intermediate 2

Intermediate 1 (0.76 g, 1.33 mmol) was dissolved in ethanol (24 ml) and subjected to catalytic hydrogenation over Lindlar Catalyst (0.095 g) for 16 h. Catalyst was removed by filtration and evaporation of solvent in vacuo gave Intermediate 2 (0.72 g, 99% yield) as a cream coloured foam. LC/MS (Method A) showed $MH^+$=545; $T_{RET}$=2.24 min Intermediate 2 (0.72 g, 1.32 mmol) was dissolved in tetrahydrofuran (7 ml) and treated with N,N'-bis-(tert-butoxycarbonyl)-1-guanylpyrazole (0.45 g, 1.45 mmol). The mixture was stirred under a nitrogen atmosphere for 16 h. Volatiles were removed in vacuo to give a solid residue which was purified by Biotage flash chromatography; eluant initially EtOAc: Cyclohexane (1:1) then EtOAc: Cyclohexane (5:3). Evaporation of solvent in vacuo afforded Intermediate 3 (0.48 g, 46% yield) as a white solid. LC/MS (Method A) showed $MH^+$=787; $T_{RET}$=3.64 min

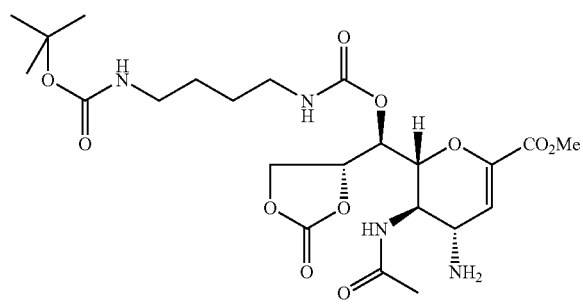

Intermediate 2

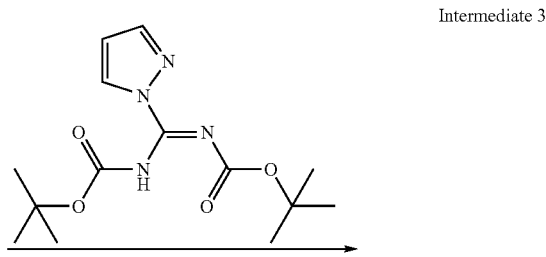

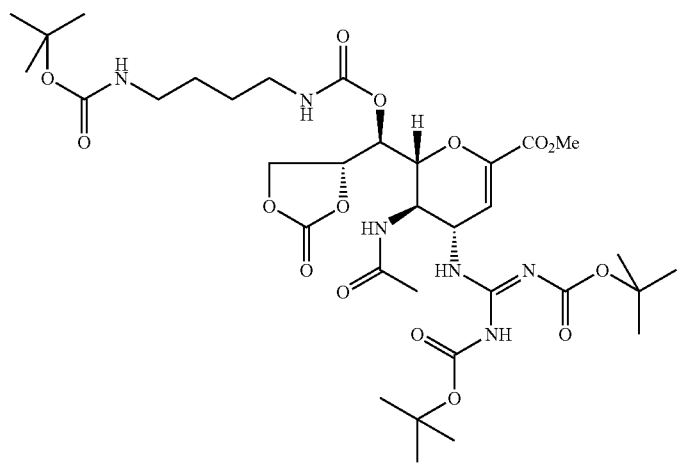

Intermediate 3

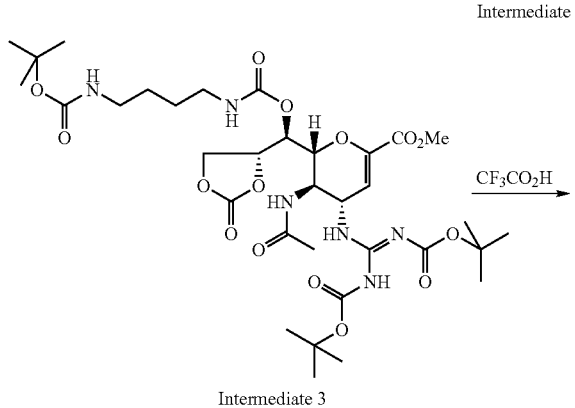

Intermediate 3

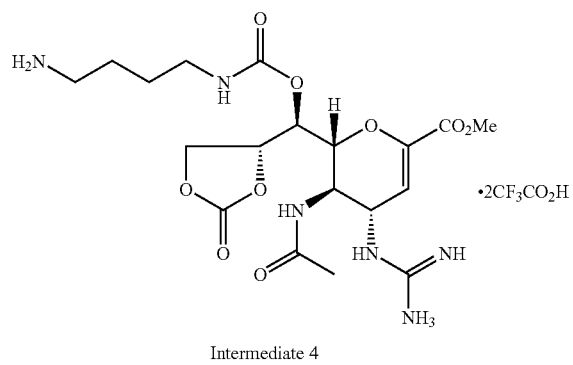

Intermediate 4

Intermediate 3 (0.48 g, 0.61 mmol) was dissolved in dichloromethane (19 ml). The solution was cooled in an ice bath and trifluoroacetic acid (19 ml) was added portionwise over 5 minutes. The mixture was then stirred for 1 h under a nitrogen atmosphere before being allowed to warm to ambient temperature and stirred a further 16 h. Volatiles were removed in vacuo, and the residue azeotroped from toluene to remove remaining trifluoroacetic acid. Trituration with diethyl ether (20 ml) afforded a white solid which was separated to give Intermediate 4 (0.50 g). LC/MS (Method B) showed (M−H)⁻=485; $T_{RET}$=0.52 min.

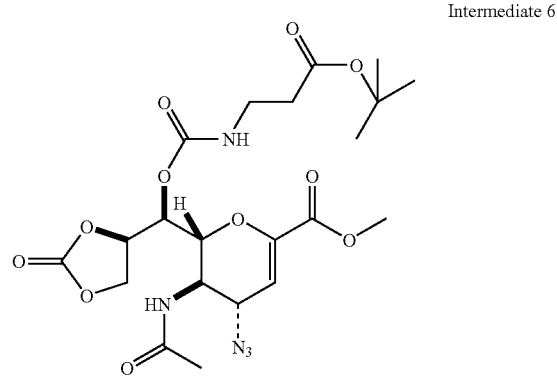

Intermediate 6

(4S, 5R, 6R)-5-Acetylamino-4-azido-6-[(S)-4-nitrophenoxycarbonyloxy)-(2-oxo-[1,3]dioxolan-4R-yl)-methyl]-5,6-dihydro-4H-pyran-2-carboxylic acid methylester (see *Eur. J. Med. Chem.* 1999, 34, 563–574) (4.0 g) was azeotroped with toluene (50 mL) and dissolved in MeCN (40 mL) and triethylamine (1.12 mL) and 3-aminopropionic acid t-butyl ester hydrochloride (1.396 g) added. After 3 days at RT, the solvent was removed and the residue diluted with EtOAc (150 mL). This was washed with 5% citric acid solution (2×50 mL), dried (MgSO₄) and concentrated. Purification by Biotage eluting with 1:1 cyclohexane: EtOAc, then 60:40 then 65:35 cyclohexane: EtOAc gave Intermediate 6 as a colourless foam (3.45 g).

¹H-NMR (400 MHz, CDCl₃) δ 6.72 (d, 1H), 5.97 (d, 1H), 5.53 (t, 1H), 5.40 (t, 1H), 5.03–4.95 (m, 2H), 4.92 (dd, 1H), 4.74–4.64 (m, 2H), 3.83 (s, 3H), 3.64–3.54 (m, 1H), 3.38–3.27 (m, 2H), 2.65–2.56 (m, 1H), 2.52–2.43 (m, 1H), 2.06 (s, 3H), 1.70 (s, 1H), 1.48 (s, 9H).

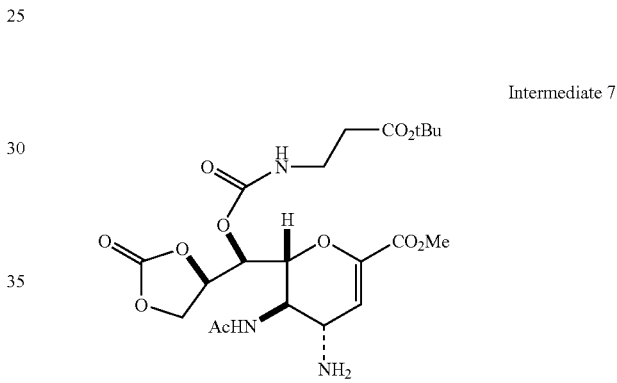

Intermediate 7

Similarly prepared to Intermediate 2 from Intermediate 6.
LC/MS (green method) MH⁺504, $T_{RET}$=2.22 min Intermediate 8

Intermediate 8 was prepared similarly to Intermediate 3 from Intermediate 7
LC/MS (green method) MH⁺744, $T_{RET}$=3.66 min

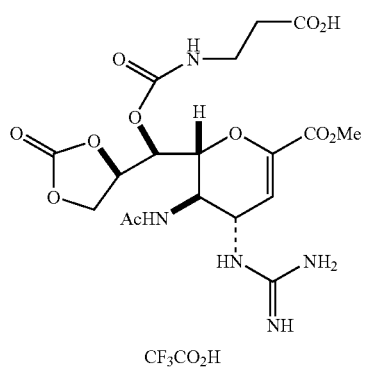

Intermediate 9

Intermdiate 8 (1.44 g), trifluoroacetic acid (20 mL), dichloromethane (20 mL) and anisole (2 mL) were stirred at RT for 3 h after which the volatiles were removed in vacuo. The residue was triturated with $Et_2O$ (2×25 mL) and then dried in vacuo to afford Intermediate 9 as a white solid (1.22 g).

LC/MS (green method) $MH^+$ 488, $T_{RET}$=1.25 min

EXAMPLE 1

Preparation of Compound 9 by Reaction of Intermediate 5 and Succinic Acid

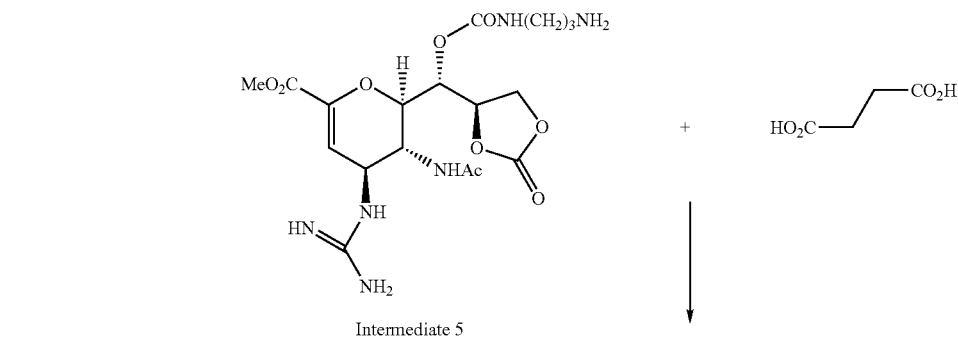

Intermediate 5

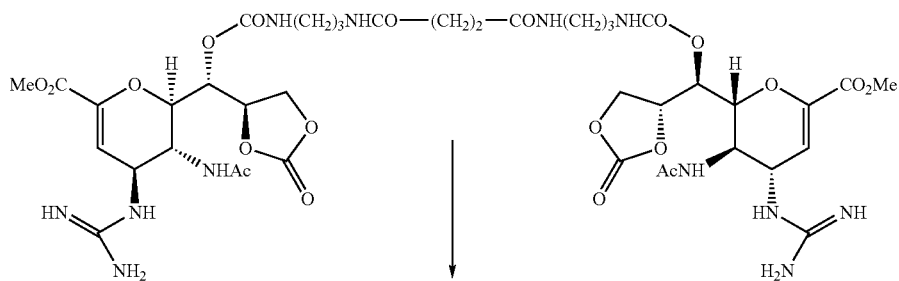

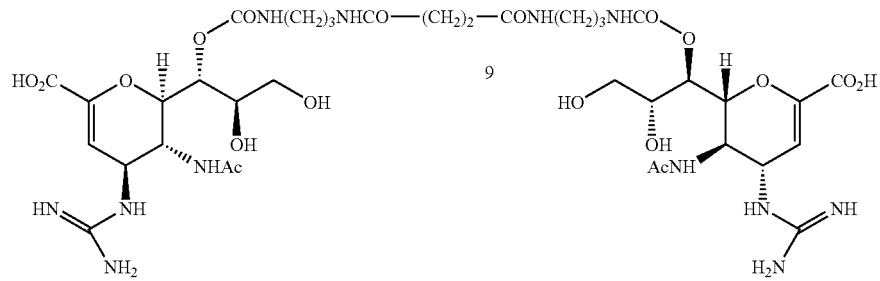

The aminopropyl Intermediate 5 was prepared following a similar sequence of steps to that described for the analogous aminobutyl Intermediate 4.

Succinic acid (4.21 mg, 0.0357 mmole), Intermediate 5 (50 mg, 0.071 mmole) and benzotriazol-1-yloxy-tris(dimethylamino)phosphonium hexafluorophosphate (BOP) (37.7 mg, 0.0852 mmole) were dissolved in DMF (2 ml) to which was added di-isopropylethylamine (DIPEA, 91.8 mg, 0.71 mmole). The resulting mixture was stirred at room temperature for 5 hours. The reaction mixture was purified by reverse phase HPLC using a Waters Symmetry C18 column (5 micron 19×100 mm), and gradient elution as shown in the following Table, to afford the protected dimer (12.8 mg, 35%), MS 1027.4 $(M+H)^+$

| Time (minutes) | A % | B % | Flow rate (ml/min) |
| --- | --- | --- | --- |
| 0 | 100 | 0 | 6 |
| 2 | 100 | 0 | 6 |
| 22 | 40 | 60 | 6 |
| 32 | 40 | 60 | 6 |
| 35 | 100 | 0 | 6 |
| 42 | 100 | 0 | 6 |

A=Water containing 0.1% trifluoroacetic acid
B=Acetonitrile containing 0.06% trifluoroacetic acid The protected dimeric compound (12.5 mg, 0.0121 mmole) was dissolved in a mixture of water/methanol/triethylamine in the ratio 4:4:1 (1.5 ml) and stirred at room temperature for 1 hour then evaporated to dryness under reduced pressure. Remaining triethylamine was removed by repeated addition of water and evaporation under reduced pressure. The remaining residue was purified by reverse phase HPLC using a Waters Symmetry C18 column (5 micron, 19×100 mm), and gradient elution as shown in the following Table, to afford the dimer 9 as a white solid (7.5 mg, 65%) after freeze-drying.

| Time (minutes) | A % | B % | Flow rate (ml/min) |
| --- | --- | --- | --- |
| 0 | 100 | 0 | 6 |
| 2 | 100 | 0 | 6 |
| 22 | 60 | 40 | 6 |
| 32 | 60 | 40 | 6 |
| 35 | 100 | 0 | 6 |
| 42 | 100 | 0 | 6 |

A = Water containing 0.1% trifluoroacetic acid
B = Acetonitrile containing 0.06% trifluoroacetic acid

MS 474.4 $(M+2H)^{2+}$, 946.8 $(M+H)^+$ $^1$H-nmr (D$_2$O) δ (ppm): 1.64 (br, 4H); 1.94 (s, 6H); 3.06 (br, 4H); 3.17 (m, 6H); 3.48 (dd, 2H); 3.63 (dd, 2H); 4.05 (m, 2H); 4.10 (dd, 2H); 4.39 (dd, 2H); 4.49 (dd, 2H); 4.91 (dd, 2H); 5.82 (d, 2H).

EXAMPLE 2

Compounds Numbered 1–8, 10–14 and 21–25 in Table 1 were each prepared by coupling the correct aminoalkyl compound (eg Intermediate 4 or 5) with the appropriate dicarboxylic acid following similar conditions to those described in Example 1.

EXAMPLE 3

Compounds Numbered 15–18 in Table 1 were prepared from the carboxy Intermediate 9 by coupling with the appropriate diamine and then deprotection following similar conditions to that given in Example 1. Compounds Numbered 19 and 20 in Table 1 were prepared from coupling of the glycine carboxy analog of Intermediate 9 with the appropriate diamine.

EXAMPLE 4

Evaluation of the Compounds of Formula (I)—Inhibition of Influenza Virus Replication Cytopathic effect (CPE) assays were performed essentially as described by Watanabe et al. (J. Virological Methods, 1994 48 257). MDCK cells were infected with a defined inoculum of virus (determined by experimentation to be the minimum sufficient to cause adequate CPE in 72 hours and to be susceptible to control compounds at concentrations considered to be consistent with published norms) in the presence serial dilutions of Compounds of the invention. Cultures were incubated for up to 72 hours at 37° C. in a 5% $CO_2$ atmosphere. The extent of CPE and hence viral replication was determined via metabolism of the viral dye 3-(4,5-dimethylthiazol-2-yl)-2,5-diphenyltetrazolium bromide (MTT) according to published methods (see for example, Watanabe et al., 1994). The compound concentration that inhibited CPE by 50% ($ID_{50}$) was calculated using a computer program for curve fitting. Influenza A/Sydney/5/97 and B/Haribin/7/95 viruses were assayed and the results are shown in Table 1. Comparable data for a specifically disclosed compound in WO 00/55149 and for compound A is also shown in Table 1.

TABLE 1

| Description | $ID_{50}$ µg/ml A/Sydney/5/97+ | $ID_{50}$ µg/ml B/Harbin/7/95 |
| --- | --- | --- |
| Compound A | 0.023 +/− 0.024 | 0.013 +/− 0.011 |
| Compound 1 | 0.0007 | 0.009 |
| Compound 2 | 0.0003 | 0.003 |
| Compound 3 | 0.0003 | 0.002 |
| Compound 4 | 0.0003 | 0.001 |
| Compound 5 | 0.0005 | 0.0009 |
| Compound 6 | 0.0008 | 0.005 |
| Compound 7 | 0.0003 | 0.001 |
| Compound 8 | 0.0004 | 0.001 |
| Compound 9 | 0.0003 | 0.0003 |
| Compound 10 | 0.0006 | 0.0007 |
| Compound 11 | 0.0003 | 0.0003 |
| Compound 12 | 0.0005 | 0.0002 |
| Compound 13 | 0.0003 | 0.0002 |
| Compound 14 | 0.0003 | 0.0002 |
| Compound 15 | >0.1 | 0.0002 |
| Compound 16 | 0.0005 | 0.0003 |
| Compound 17 | >0.1 | 0.0004 |
| Compound 18 | 0.0003 | 0.0003 |
| Compound 19 | >0.1 | 0.0002 |
| Compound 20 | >0.1 | 0.00005 |
| Compound 21 | 0.0002 | 0.0003 |
| Compound 22 | 0.0002 | 0.0003 |
| Compound 23 | 0.0002 | 0.0003 |

TABLE 1-continued

| Description | ID$_{50}$ μg/ml A/Sydney/5/97+ | ID$_{50}$ μg/ml B/Harbin/7/95 |
|---|---|---|
| Compound 24 | 0.0002 | 0.0007 |
| Compound 25 | 0.0001 | 0.0003 |
| Compound Number 8* | 0.0007, 0.0005 | 0.007 +/− 0.01 |
| Compound Number 10* | 0.057 | >0.1 |

*As referenced in WO 00/55149

+ Data provided in WO 00/55149 related to the virus H3N2 isolate A/Victoria/3/75 rather than A H3N2 isolate A/Sydney/5/97. When comparing such data the person skilled in the art will appreciate that differences in antiviral potency are not uncommon for a given compound when analysed against several different viruses in vitro. For example, Woods et al (Antimicrob Agents Chemother 1993 37:1473–9) have reported that Compound A exhibits a wide range of EC50 values (from 0.02 to 0.16 uM) in in vitro assays involving recent clinical isolates. Accordingly, compound 8 was found to be more potent in CPE assays involving the recent influenza A H3N2 isolate. A/Sydney/5/97 than the earlier H3N2 isolate A/Victoria/3/75.

Data provided in Table 1 demonstrate that the compounds 1–25, in addition to being substantially more potent than the highly active compound A, are even more potent against A/Sydney/5/97 and substantially more potent against the recent influenza B isolate B/Harbin/7/95 than compounds 8 and 10 of WO 00/55149.

EXAMPLE 5

Plaque Reduction Assay

Madin Darby Canine Kidney (MDCK) cells are seeded into six well tissue culture plates and grown to confluency via standard methods. Influenza viruses are diluted in a minimal volume of phosphate buffered saline supplemented with 0.2% bovine serum albumin to yield an estimated titre of 50–100 plaque forming units (pfu) per well. After adsorption to the MDCK cells for one hour at 37° C. in a 5% $CO_2$ atmosphere the viral inocula is aspirated and replaced with viral growth media (minimal Eagle's media supplemented with BSA, trypsin and insulin/transferrin/selenium at optimal concentrations) containing sufficient agar or agarose (generally. 1–2%) to cause the media to gel at room temperature and at 37° C. in a 5% $CO_2$ atmosphere until plaques develop (generally 2–4 days). Plaques can be visualised with a suitable stain (e.g. 0.4% crystal violet in formal saline) before counting. Antiviral potency is expressed as the concentration of test article which reduces plaque numbers by 50% of the untreated control value ($EC_{50}$).

| | EC$_{50}$ ng/ml PRA | | | | |
|---|---|---|---|---|---|
| Example | A/WSN* | A/Vic* | A/Syd* | A/New* | A/Pan* |
| Compound A | 56, >100 | 5.5 +/− 8.2 | 2.4 | 0.27, 0.23 | 2.7, 3 |
| 1 | 0.05 | <0.01, 0.006, 0.08, 0.21 | 0.02, 0.001 | 0.03, 0.13 | >1 |
| Amantadine | | 220 | | 11 | 157 |
| Oseltamivir | | 0.11 | | 0.23 | 0.3 |

*A/WSN/33 BVLV09 (H1N1)
A/Victoria/3/75 BVLV017 (H3N2)
A/Sydney/5/97 BVLV015 (H3N2)
A/New Caledonia/20/99 BVLV008 (H1N1)
A/Panama/2007/99 BVLV008 (H3N2)
A/Bayern/7/95 BVL006 (H1N1)

| | EC$_{50}$ ng/ml PRA | | | |
|---|---|---|---|---|
| Example | B/Vic* | B/Harb* | B/HongK* | B/Yam* |
| Compound A | 3, 20 | 0.19 | 21 +/− 6 | 0.2, 3.1 |
| 1 | <0.01, 0.1 | 0.014 | 0.316 | 0.032 |
| Amantadine | | | >10000 | 2061 |
| Oseltamivir | | | 32 | 0.7 |

*B/Victoria/1/67
B/Hong Kong/5/72 BVLV012
B/Harbin/7/95 BVLV008
B/Yamanashi/166/98 BVLV007

EXAMPLE 6

Assessment of Long Duration of Action

Rodents are anaesthetised and dosed with compound of interest by the intra-tracheal route at a dose volume of 0.8 ml/kg. The rodent is then held in the vertical position until full recovery is achieved. At different time points, for example, 2, 8, 24 and 48 hours post-dose, levels of compound in the lung tissue are assessed by analytical methods. Any analytical method suitable for detection of this type of compound may be used. The time at which levels of compound fall below the sensitivity of the analytical techniques identified will determine the residency time of the compound in lung tissue.

The rat lung retention data for selected compounds is shown below. Please note that all experiments included a co-dosed internal standard, namely compound 3 of International Patent Publication No. WO 02/20514, to permit comparison. The data are expressed as a ratio with respect to this compound, the structure of which is shown below.

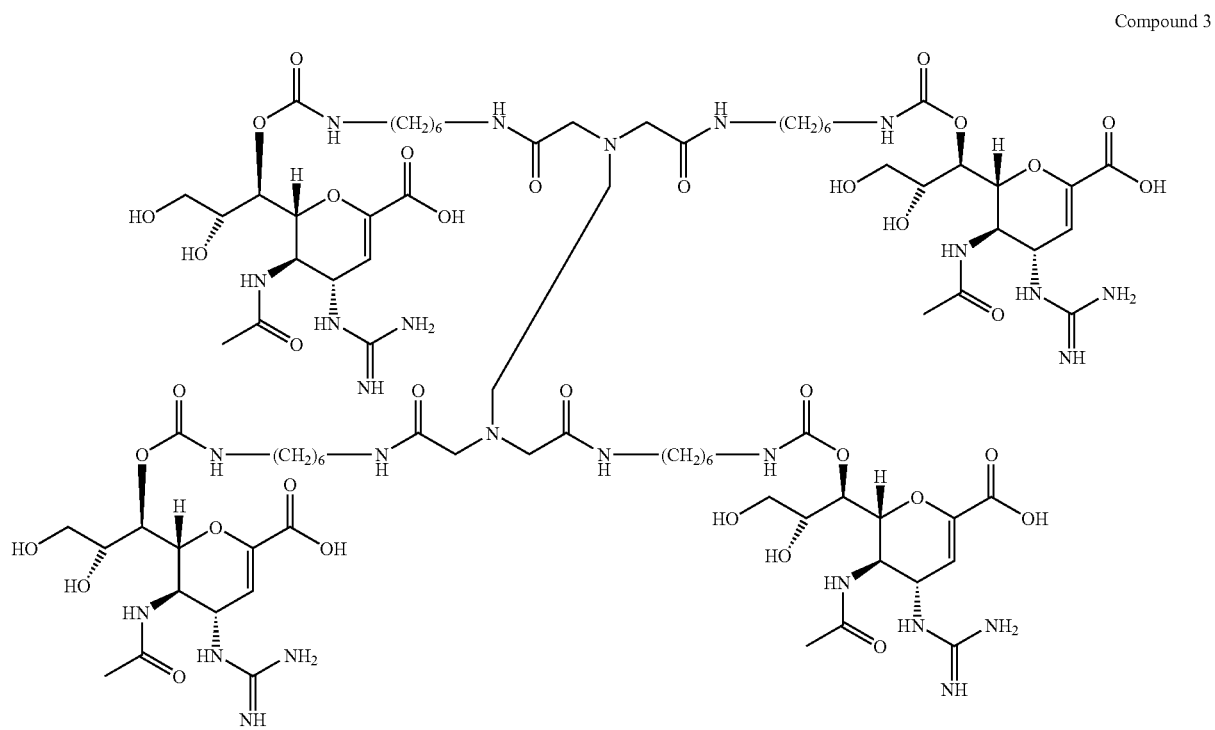

Compound 3

The data for compound A is included for comparison purposes. The compounds of the invention have significantly greater retention at 7 days than Compound A when expressed as a ratio of compound concentration to standard concentration.

| time point hrs | Compound | dose mg/kg | [cmpd] ng/g | Mean [cmpd] ng/g | (PCT AU01/01128 Compound 3) ng/g | Mean (PCT AU01/01128 Compound 3) ng/g | Ratio Mean [lung] [cmpd]/PCT AU01/01128 compound 3 |
|---|---|---|---|---|---|---|---|
| 48 | Compound 18 | 0.1 | 565 | 442 | 607 | 608 | 0.73 |
| 48 | Compound 18 | 0.1 | 294 | | 363 | | |
| 48 | Compound 18 | 0.1 | 467 | | 855 | | |
| 168 | Compound 18 | 0.1 | 150 | 161 | 351 | 349 | 0.46 |
| 168 | Compound 18 | 0.1 | 98 | | 243 | | |
| 168 | Compound 18 | 0.1 | 234 | | 451 | | |
| 48 | Compound A (zanamivir) | 0.1 | 421 | 352 | 698 | 1368 | 0.26 |
| 48 | Compound A (zanamivir) | 0.1 | 369 | | 1901 | | |
| 48 | Compound A (zanamivir) | 0.1 | 267 | | 1507 | | |
| 168 | Compound A (zanamivir) | 0.1 | 91 | 61 | 815 | 750 | 0.08 |
| 168 | Compound A (zanamivir) | 0.1 | 47 | | 925 | | |
| 168 | Compound A (zanamivir) | 0.1 | 45 | | 512 | | |

EXAMPLE 7

Alternative Assessment of Long Duration of Action and Efficacy

The protocol for infecting mice has been described previously (1–4). Mildly anaesthetised mice are inoculated into the external nares with influenza virus. Treatment procedure and regimen. A single dose of compound is administered at a defined time point up to 10 days prior to infection, preferably 4–7 days prior to infection, or following infection, preferably immediately following infection and up to 48 hours post infection. In most experiments, a non-lethal strain of influenza is used, and efficacy is assessed by reductions in lung virus titre. For mice given compound prior to infection, lungs are removed post infection either on a single day, or on days following infection, preferably days 1–4 post infection. Homogenised lung samples are assayed for virus using established methods, and the titres of viral load estimated and compared to titres of virus in lungs of untreated mice.

In those experiments where a mouse-adapted lethal strain of influenza is used, efficacy is assessed by an increase in survival rate and/or numbers of survivors, as compared to untreated mice.

REFERENCES

1. Ryan, D. M., J. Ticehurst, M. H. Dempsey, and C. R. Penn, 1994. Inhibition of influenza virus replication in mice by GG167 (4-guanidino-2,4-dideoxy-2,3-dehydro-N-acetylneuraminic acid) is consistent with extracellular activity of viral neuraminidase (sialidase). Antimicrob. Agents and Chemother. 38 (10):2270–2275.
2. von Itzstein M., W.-Y. Wu, G. B. Kok, M. S. Pegg, J. C. Dyason, B. Jin, T. V. Phan, M. L. Smythe, H. F. White, S. W. Oliver, P. M. Colman, J. N. Varghese, D. M. Ryan, J. M. Woods, R. C. Bethell, V. J. Hogham, J. M. Cameron, and C. R. Penn. 1993. Rational design of potent sialidase-based inhibitors of influenza virus replication. Nature (London) 363:418–423.
3. Woods, J. M., R. C. Bethell, J. A. V. Coates, N. Healey, S. A. Hiscox, B. A. Pearson, D. M. Ryan, J. Ticehurst, J. Tilling, S. A. Walcott, and C. R. Penn. 1993. 4-Guanidino-2,4-dideoxy-2,3-dehydro-N-acetylneuraminic acid is a highly effective inhibitor both of the sialidase (neuraminidase) and of growth of a wide range of influenza A and B viruses in vitro. Antimicrob. Agents Chemother. 37:1473–1479.
4. Robert J Fenton, Peter J Morley, Ian J Owens, David Gower, Simon Parry, Lee Crossman and Tony Wong (1999). Chemoprophylaxis of influenza A virus infections, with single doses of zanamivir, demonstrates that zanamivir is cleared slowly from the respiratory tract. Antimicrob. Agents and Chemother. 43, 11, 2642–2647.

What is claimed is:

1. A compound of general formula (I):

(I)

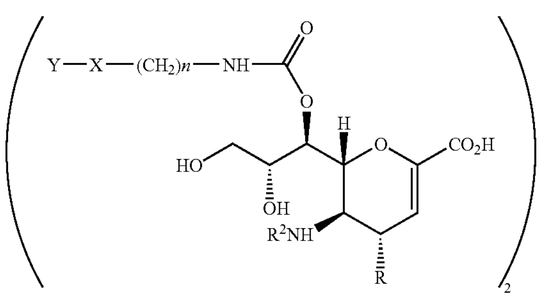

in which

R is an amino or guanidino group;

$R^2$ is acetyl or trifluoroacetyl;

X is CONH, NHCO or O;

n is an integer from 2 to 6; and

Y is $C_2$–$C_8$ alkyl, $C_3$–$C_8$ cycloalkyl, $C_1$–$C_4$ alkoxyalkyl, an amino acid or dipeptide, or a pharmaceutically acceptable salt, ether, ester or salt of such ester thereof, with the proviso that when R is a guanidino group, $R^2$ is acetyl, X is O and n is 2, then Y is not $C_2$ alkyl.

2. A compound according to claim 1, in which R is a guanidino group.

3. A compound according to claim 1, in which $R^2$ is an acetyl group.

4. A compound according to claim 1, which contains a pharmaceutically acceptable salt, ether, ester or salt of such ester at one or more of the carboxyl groups, hydroxyl groups, amino groups or guanidine groups.

5. A compound according to claim 1, in which said compound is an alkyl ester, an aryl ester or an acetyl ester.

6. A method for the preparation of the compound of formula (I) according to claim 1 to 5 when X is CONH or NHCO, which comprises the steps of (a) coupling a compound of formula (II)

(II)

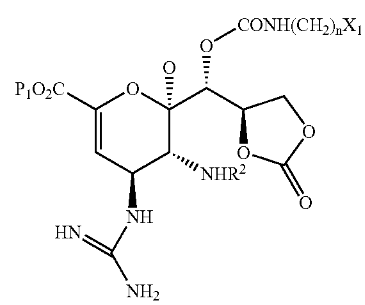

in which $R^2$ and n are as defined in claim 1, $P_1$ is a carboxylic acid protecting group and $X_1$ is $NH_2$ or $CO_2H$;

with a compound of formula (III)

$X_2$—Y—$X_2$ (III)

in which Y is as defined in claim 1 and $X_2$ is $CO_2H$ or $HN_2$ provided that it is not the same as $X_1$ to form a compound of formula (IV)

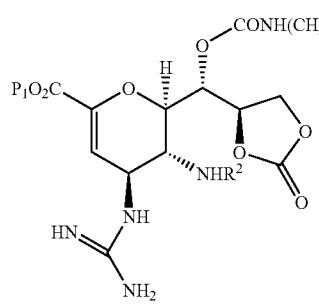 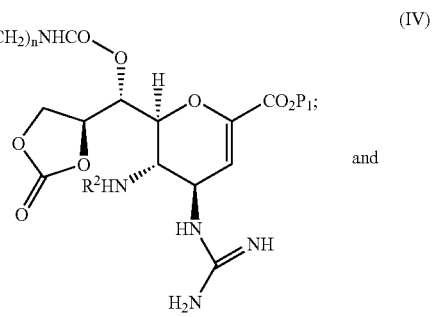

(IV)

and (b) deprotecting the compound of formula (IV).

7. A pharmaceutical formulation comprising a therapeutically effective amount of a compound of formula (I) as defined in claim 1 or a pharmaceutically acceptable salt, ether, ester or salt of such ester thereof, together with one or more pharmaceutically acceptable carriers.

8. A pharmaceutical formulation according to claim 7, which comprises one or more anti-viral agents used to treat respiratory infections.

9. A pharmaceutical formulation according to claim 8, in which the agent is zanamivir, oseltamivir, amantadine, rimantadine, and/or ribavirin.

10. An inhaler which comprises a compound according to claim 1.

11. An inhaler according to claim 10 which is adapted for oral administration as a free-flow powder.

12. An inhaler according to claim 10 which is a metered dose aerosol inhaler.

13. A method for the treatment of an orthomyxovirus or paramyxovirus infection comprising the step of administration to a subject in need thereof of an effective amount of a compound of formula (I) as defined in claim 1.

14. A method according to claim 13 in which an orthomyxovirus or paramyxovirus infection is an influenza A or B infection, parainfluenza, mumps or Newcastle disease.

15. A method according to claim 13 in which the administration is to the respiratory tract by inhalation, insufflation or intranasally or a combination thereof.

* * * * *

UNITED STATES PATENT AND TRADEMARK OFFICE
CERTIFICATE OF CORRECTION

| | | |
|---|---|---|
| PATENT NO. | : 7,223,790 B2 | |
| APPLICATION NO. | : 10/494260 | |
| DATED | : May 29, 2007 | |
| INVENTOR(S) | : Betty Jin et al. | |

It is certified that error appears in the above-identified patent and that said Letters Patent is hereby corrected as shown below:

In Column 11, Line 11, please delete "EtOAC ethyl acetate." The aforementioned compound is repeated a second time.

In Column 24, Line 32, please delete "Treatment Procedure and Regimen" and replace with -- Treatment Procedure and Regimen --.

In Column 26, Claim 6, Line 65, please delete "as defined in claim 1 and $X_2$ is $CO_2H$ or $HN_2$ provided" and replace with -- as defined in claim 1 and $X_2$ is $CO_2H$ or $NH_2$ provided --.

UNITED STATES PATENT AND TRADEMARK OFFICE
CERTIFICATE OF CORRECTION

PATENT NO. : 7,223,790 B2
APPLICATION NO. : 10/494260
DATED : May 29, 2007
INVENTOR(S) : Betty Jin et al.

It is certified that error appears in the above-identified patent and that said Letters Patent is hereby corrected as shown below:

In Claim 6, Line 1 (in the chemical structure), please delete

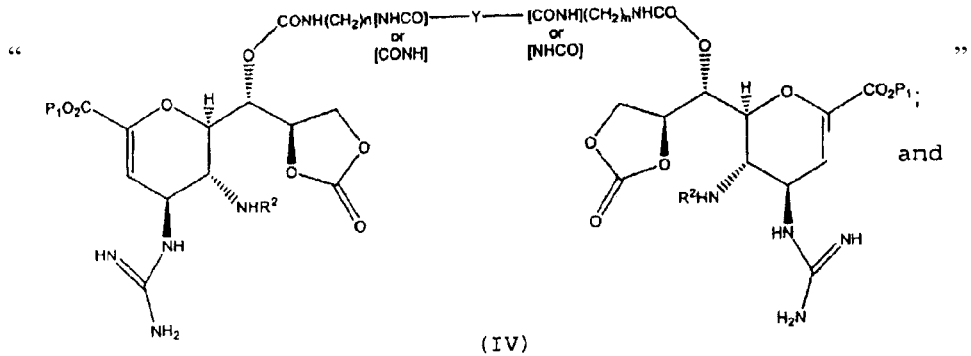

And replace with

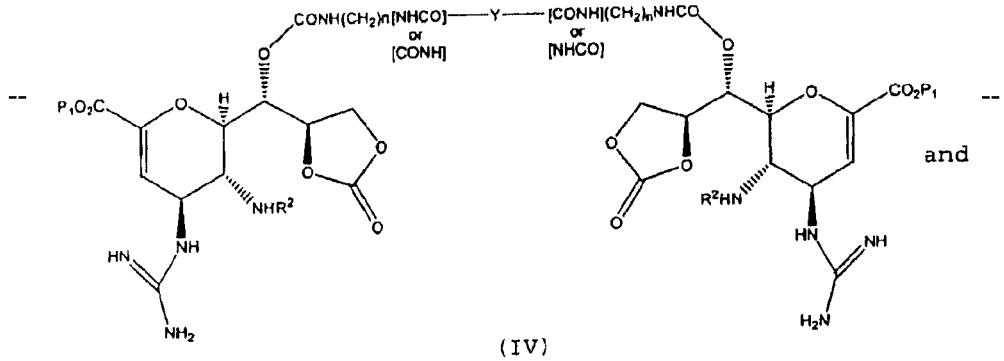

Signed and Sealed this

Fifteenth Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 7,223,790 B2
APPLICATION NO. : 10/494260
DATED : May 29, 2007
INVENTOR(S) : Betty Jin et al.

It is certified that error appears in the above-identified patent and that said Letters Patent is hereby corrected as shown below:

In Column 11, Line 11, please delete "EtOAC ethyl acetate." The aforementioned compound is repeated a second time.

In Column 24, Line 32, please delete "Treatment Procedure and Regimen" and replace with -- Treatment Procedure and Regimen --.

In Column 26, Claim 6, Line 65, please delete "as defined in claim 1 and $X_2$ is $CO_2H$ or $HN_2$ provided" and replace with -- as defined in claim 1 and $X_2$ is $CO_2H$ or $NH_2$ provided --.

Column 27, In Claim 6, Line 1 (in the chemical structure), please delete

UNITED STATES PATENT AND TRADEMARK OFFICE
CERTIFICATE OF CORRECTION

PATENT NO. : 7,223,790 B2  
APPLICATION NO. : 10/494260  
DATED : May 29, 2007  
INVENTOR(S) : Betty Jin et al.

It is certified that error appears in the above-identified patent and that said Letters Patent is hereby corrected as shown below:

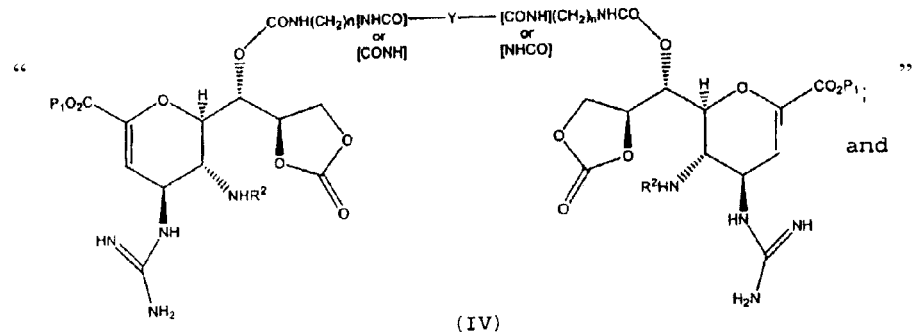

And replace with

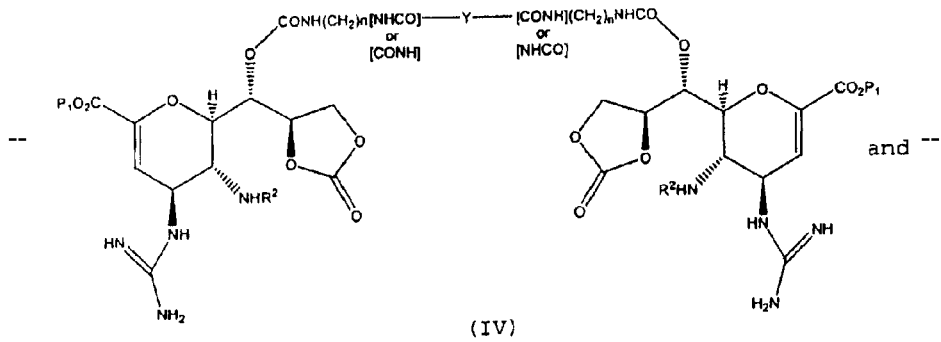

This certificate supersedes the Certificate of Correction issued July 15, 2008.

Signed and Sealed this

Fifth Day of August, 2008

JON W. DUDAS  
*Director of the United States Patent and Trademark Office*